(12) United States Patent
Fisher et al.

(10) Patent No.: US 7,938,806 B2
(45) Date of Patent: May 10, 2011

(54) TEARAWAY INTRODUCER SHEATH WITH HEMOSTASIS VALVE

(75) Inventors: Mark S. Fisher, Sellersville, PA (US); W. Shaun Wall, North Wales, PA (US)

(73) Assignee: Medical Components, Inc., Harleysville, PA (US)

( * ) Notice: Subject to any disclaimer, the term of this patent is extended or adjusted under 35 U.S.C. 154(b) by 27 days.

(21) Appl. No.: 12/402,053

(22) Filed: Mar. 11, 2009

(65) Prior Publication Data

US 2009/0234290 A1    Sep. 17, 2009

Related U.S. Application Data

(60) Provisional application No. 61/036,736, filed on Mar. 14, 2008, provisional application No. 61/102,570, filed on Oct. 3, 2008.

(51) Int. Cl.
*A61M 5/178* (2006.01)
(52) U.S. Cl. .................................. 604/167.04
(58) Field of Classification Search .................. 604/160, 604/167.01, 167.03, 167.04
See application file for complete search history.

(56) References Cited

U.S. PATENT DOCUMENTS

| | | | |
|---|---|---|---|
| 4,411,654 A | 10/1983 | Boarini et al. | |
| 4,436,519 A | 3/1984 | O'Neill | |
| 4,596,559 A | 6/1986 | Fleischhacker | |
| 4,610,665 A | 9/1986 | Matsumoto | |
| 4,655,752 A | 4/1987 | Honkanen et al. | |
| 4,747,833 A | 5/1988 | Kousai et al. | |
| 4,772,266 A | 9/1988 | Groshong | |
| 4,865,593 A | 9/1989 | Ogawa et al. | |
| 4,932,633 A | 6/1990 | Johnson et al. | |
| 4,983,168 A | 1/1991 | Moorehead | |
| 5,064,414 A | 11/1991 | Revane | |
| 5,085,645 A | 2/1992 | Purdy et al. | |
| 5,098,392 A | 3/1992 | Fleischhacker et al. | |
| 5,125,904 A | 6/1992 | Lee | |
| 5,154,701 A | 10/1992 | Cheer et al. | |

(Continued)

FOREIGN PATENT DOCUMENTS

EP        0631793 A1    1/1995

(Continued)

OTHER PUBLICATIONS

Intl Search Report dated May 8, 2009; PCT/US2009/036486 (4 pages).

(Continued)

*Primary Examiner* — Nicholas D Lucchesi
*Assistant Examiner* — Aarti B Berdichevsky
(74) *Attorney, Agent, or Firm* — Anton P. Ness; Fox Rothschild LLP

(57) ABSTRACT

A tearaway introducer sheath assembly (100,200) having an integrated valve (300). The valve is seated within a valve housing (222) defined by the hub portion (200) of the sheath (200). The valve (300) includes a pair of distally extending opposed side walls or flaps (324) extending to converge at a distal tip (328) having a virtual opening (334) therethrough. The valve further includes a pair of tensioners (340) along outer surfaces of the opposed side walls (324) that extend radially outwardly to engage and bear against the interior valve housing surface (230) to press the opposed side walls (324) together at the distal tip (328) for sealing, both when a dilator extends through the valve and sheath and afterward upon removal of the dilator.

11 Claims, 8 Drawing Sheets

U.S. PATENT DOCUMENTS

| | | | |
|---|---|---|---|
| 5,167,634 | A | 12/1992 | Corrigan, Jr. et al. |
| 5,207,649 | A | 5/1993 | Aruny |
| 5,221,263 | A | 6/1993 | Sinko et al. |
| 5,250,033 | A | 10/1993 | Evans et al. |
| 5,269,771 | A | 12/1993 | Thomas et al. |
| 5,304,142 | A | 4/1994 | Liebl et al. |
| 5,312,355 | A | 5/1994 | Lee |
| 5,350,363 | A | 9/1994 | Goode et al. |
| 5,397,311 | A | 3/1995 | Walker et al. |
| 5,411,483 | A | 5/1995 | Loomas et al. |
| 5,423,762 | A | 6/1995 | Hillstead |
| 5,441,504 | A | 8/1995 | Pohndorf et al. |
| 5,456,284 | A | 10/1995 | Ryan et al. |
| 5,458,640 | A | 10/1995 | Gerrone |
| 5,613,953 | A | 3/1997 | Pohndorf |
| 5,720,759 | A | 2/1998 | Green et al. |
| 5,755,693 | A | 5/1998 | Walker et al. |
| 5,885,217 | A | 3/1999 | Gisselberg et al. |
| 5,911,710 | A | 6/1999 | Barry et al. |
| 6,024,729 | A | 2/2000 | Dehdashtian et al. |
| 6,080,174 | A | 6/2000 | Dubrul et al. |
| 6,083,207 | A | 7/2000 | Heck |
| 6,197,016 | B1 | 3/2001 | Fourkas et al. |
| 6,277,100 | B1 | 8/2001 | Raulerson et al. |
| D450,839 | S | 11/2001 | Junker |
| 6,322,541 | B2 | 11/2001 | West et al. |
| 6,336,914 | B1 | 1/2002 | Gillespie, III |
| 6,454,744 | B1 | 9/2002 | Spohn et al. |
| 6,488,674 | B2 | 12/2002 | Becker et al. |
| 6,562,049 | B1 | 5/2003 | Norlander et al. |
| 6,589,262 | B1 | 7/2003 | Honebrink et al. |
| 6,623,460 | B1 | 9/2003 | Heck |
| 6,712,789 | B1 | 3/2004 | Lange et al. |
| 6,712,791 | B2 | 3/2004 | Lui et al. |
| 6,764,464 | B2 | 7/2004 | McGuckin, Jr. et al. |
| 6,796,991 | B2 | 9/2004 | Nardeo |
| 6,808,509 | B1 | 10/2004 | Davey |
| 6,827,710 | B1 | 12/2004 | Mooney et al. |
| 6,837,873 | B1 | 1/2005 | Polley et al. |
| 6,916,051 | B2 * | 7/2005 | Fisher ........................... 285/373 |
| 6,966,896 | B2 | 11/2005 | Kurth et al. |
| 7,008,404 | B2 | 3/2006 | Nakajima |
| 7,101,353 | B2 | 9/2006 | Lui et al. |
| 7,192,433 | B2 | 3/2007 | Osypka et al. |
| 7,390,316 | B2 * | 6/2008 | McFarlane ............... 604/167.03 |
| 7,422,571 | B2 | 9/2008 | Schweikert et al. |
| 7,744,571 | B2 * | 6/2010 | Fisher et al. ............. 604/167.04 |
| 2003/0085373 | A1 | 5/2003 | Dehdashtian |
| 2003/0088264 | A1 | 5/2003 | Spohn et al. |
| 2004/0059296 | A1 | 3/2004 | Godfrey |
| 2004/0102738 | A1 | 5/2004 | Dikeman et al. |
| 2004/0143219 | A1 | 7/2004 | Lee et al. |
| 2004/0183305 | A1 * | 9/2004 | Fisher ........................... 285/419 |
| 2004/0193119 | A1 | 9/2004 | Canaud et al. |
| 2004/0267202 | A1 | 12/2004 | Potter |
| 2005/0010238 | A1 | 1/2005 | Potter et al. |
| 2005/0027282 | A1 * | 2/2005 | Schweikert et al. .......... 604/523 |
| 2005/0043684 | A1 | 2/2005 | Basta et al. |
| 2005/0080398 | A1 * | 4/2005 | Markel et al. ................. 604/508 |
| 2005/0113757 | A1 * | 5/2005 | McFarlane ............... 604/167.03 |
| 2005/0267487 | A1 | 12/2005 | Christensen et al. |
| 2006/0149293 | A1 | 7/2006 | King et al. |
| 2007/0106262 | A1 | 5/2007 | Becker et al. |
| 2007/0123825 | A1 | 5/2007 | King et al. |
| 2007/0265597 | A1 * | 11/2007 | Schweikert et al. .......... 604/533 |
| 2009/0018508 | A1 * | 1/2009 | Fisher et al. ............. 604/167.04 |
| 2009/0030426 | A1 * | 1/2009 | Zinn et al. ..................... 606/108 |
| 2009/0143739 | A1 | 6/2009 | Nardeo |
| 2009/0234290 | A1 * | 9/2009 | Fisher et al. ............. 604/164.05 |
| 2009/0292253 | A1 * | 11/2009 | Raulerson et al. ....... 604/167.04 |

FOREIGN PATENT DOCUMENTS

| | | |
|---|---|---|
| EP | 1634615 A1 | 3/2006 |
| WO | WO 97/14456 | 4/1997 |
| WO | 99/45996 | 9/1999 |
| WO | WO 2005/013807 | 2/2005 |

OTHER PUBLICATIONS

Written O4pinion, dated May 8, 2009; PCT/US2009/036486 (7 pages).

Office Action dated Sep. 9, 2009; U.S. Appl. No. 12/144,297 (23 pages).

Office Action dated Oct. 5, 2009; U.S. Appl. No. 12/283,933 (18 pages).

Office Action dated Mar. 23, 2010; U.S. Appl. No. 12/283,933 (7 pages).

International Preliminary Report dated Sep. 23, 2010; PCT/US2009/036486 (9 pages).

* cited by examiner

TEARAWAY INTRODUCER SHEATH WITH HEMOSTASIS VALVE

CROSS-REFERENCE TO RELATED APPLICATIONS

This application claims priority from U.S. Provisional Patent Application Ser. No. 61/036,736, filed Mar. 14, 2008 and Ser. No. 61/102,570, filed Oct. 3, 2008.

FIELD OF THE INVENTION

This relates to the field of medical devices and more particularly to vascular catheter introducer sheaths.

BACKGROUND OF THE INVENTION

Catheters for the introduction or removal of fluids may be located in various venous locations and cavities throughout the body of a patient. One important application of catheterization is for hemodialysis. Such catheterization may be performed by using a single catheter having multiple lumens, and a typical example of such a catheter is a dual lumen catheter in which one lumen introduces fluid and the other lumen removes fluid simultaneously therewith. An example of such a multiple catheter is the SPLIT CATH® catheter, sold by Medical Components, Inc. of Harleysville, Pa. Catheterization may also be performed by using a multiple lumen assembly consisting of separate, single lumen catheters inserted through one or two different incisions into an area to be catheterized, and an example of such a multiple lumen assembly is the TESIO® catheter, also sold by Medical Components, Inc.

Generally, to insert any catheter into a blood vessel, the vessel is identified by aspiration with a long hollow needle in accordance with the well known Seldinger technique. A thin guide wire is first introduced, typically through a syringe needle or other introducer device into the interior of a blood vessel. The needle or introducer device is then removed, leaving the distal end portion of the guide wire within the vessel and the proximal end portion projecting beyond the surface of the skin of the patient.

Several options are available to a physician for catheter placement. If the catheter to be inserted is significantly larger than the guide wire, an introducer sheath with a dilator device extending therethrough is passed over the guide wire to enlarge the vessel incision hole, or venotomy. After the venotomy is sufficiently enlarged, the dilator is removed, leaving the introducer sheath and guide wire in position inserted into the venotomy. The catheter is then inserted into the sheath, through the incision and into the blood vessel, and the sheath is then removed from around the exterior of the catheter by being split apart and peeled therefrom.

A tearaway introducer sheath that can be split away from the catheter as the sheath is being removed from the patient greatly facilitates the removal of the sheath. By splitting the sheath along its longitudinal axis as the sheath is being removed from the patient, the practitioner will be able to pull out the sheath in such a way that the portion removed from the patient is split, thereby not interfering with any hubs, luer fittings, clamps, cuffs or other accessories assembled to the catheter. For tearaway introducer sheaths having sheath tubes of polytetrafluoroethylene (PTFE), the polymeric material inherently contains longitudinally oriented molecules that easily split therealong with the hub component affixed to the sheath's tube. For tearaway sheaths of polyurethane, the sheath tubes are manufactured in a way that aids in the tearing of the sheath at two opposing angular locations on the circumference of the sheath, thereby splitting the sheath into two halves separated longitudinally through the center of the sheath; a conventional manner of manufacturing polyurethane sheaths is to provide a pair of opposed score lines along the sheath's tube.

An introducer sheath is generally constructed with a hub component affixed to the sheath's tube at its proximal end. The hub serves as a handle, and as a mating point for the insertion and locking of the dilator device. When a sheath needs to be split apart to be successfully withdrawn from the patient's body while leaving the catheter in place, the hub will also have to be split apart in order to clear the catheter. The hub generally is so made to have a pair of opposed laterally extending grippable wings or tabs for splitting, as well as longitudinally extending lines of weakness, such as opposed V-grooves or reveals, that are aligned with the score lines of the sheath tube, if any.

A dilator is often used to aid in the insertion of the sheath, and has a long tubular section, the outside diameter of which is slightly smaller than the inside diameter of the sheath. The dilator also has a pointed tip on its distal end and a hollow longitudinal passageway running the entire length thereof. The dilator is inserted into the patient's body through the sheath along the guide wire, allowing the distal tip to extend into the venotomy, carefully enlarging it. The dilator is then removed along the guide wire prior to insertion of the catheter along the guide wire and into the sheath.

However, after the dilator is removed, and before the catheter is inserted through the sheath, the sheath becomes an open conduit, allowing blood to spurt from the vessel through the sheath or allowing air to be aspirated into the vessel through the sheath, neither of which is desirable or permissible. The practitioner conventionally has had to place a thumb or finger over the proximal opening of the sheath to prevent blood loss and air embolism; however, this restricts the practitioner's hand movement, and is not a reliable method. Other sheath designs attempt to solve this problem by utilizing plugs or clamps. These designs require a modification of the standard catheterization technique and are usually cumbersome to use.

It is desirable to provide a tearaway sheath having an integrated valve such that after dilator removal, the valve prevents blood or air passing through and from the sheath, prior to insertion of the catheter.

It would also be desirable to provide an integrated valve that operates automatically to close and seal the opening as soon as the dilator is removed.

It would be further desirable to provide an integrated valve that provides an audible signal as it closes thereby notifying the practitioner that the valve is closed.

BRIEF SUMMARY OF THE INVENTION

Briefly, the present invention is a tearaway catheter introducer sheath for the catheterization of a blood vessel, comprising a sheath tube and a sheath hub and containing a valve disposed therein. The sheath hub includes a pair of grippable tabs to facilitate splitting apart along longitudinal V-grooves aligned with score lines (if any) of the sheath tube, with the V-grooves forming a boundary between hub half-portions. The sheath hub defines a valve housing or seat between its half-portions, in communication with the sheath tube passageway and a proximal hub opening. The sheath tube, the sheath hub and the valve can be said to have planes of separation intersecting each thereof at respective lines of separation or weakness, that are co-aligned when the planes of separation coincide upon assembly to facilitate splitting.

The valve of the present invention includes a cylindrical wall encircling a center passageway allowing insertion therethrough, in sequence, of the guide wire, a dilator and a catheter. Preferably, the valve is generally of a duckbill shape having two essentially flat valve flaps at the distal end of the valve, the two valve flaps connecting laterally with the cylindrical side wall to circumscribe the center passage and extending longitudinally being joined to each other at side edges. The distal ends of the two flaps meet and form a tapered tip comprising a flat land having a slit formed along and through the flat land and thereacross. The cylindrical side wall is provided with one or more tear seams along the longitudinal axis of the valve including the joined side edges of the flaps, forming a boundary between half-portions of the valve. The valve is seated within the valve housing defined by the sheath hub and its half-portions are coupled to respective ones of the hub half-portions such that the valve will become split apart into its half-portions when the sheath hub and sheath tube are being split. An annular flange of the valve is defined near its proximal end for providing sealing of the valve housing upon complete sheath assembly.

A cap or caps are affixed to the proximal hub end to retain the valve in the valve housing after assembly, and also to define a lock with the dilator. Preferably, the cap comprises a pair of cap halves not joined to each other but facing each other along a longitudinal separation plane (a gap) aligned with the V-grooves of the sheath hub and valve, and which are coupled to respective ones of the sheath hub half-portions, to facilitate splitting of the sheath assembly. Retention of the valve can be said to be by way of axially extending annular flanges of the cap halves and the hub half-portions received into corresponding complementary grooves into the annular flange of the valve.

An important aspect of the present invention is that the valve also includes a pair of tensioners each positioned on a respective exterior side surface of each of the valve flaps, and that are permanently in engagement with, and cooperate with, the adjacent side walls of the valve housing to press the valve flaps radially inwardly to close the valve's slit against the guide wire or dilator or catheter extending through the slit, or to close the valve's slit completely immediately upon withdrawal of the dilator from the sheath assembly. Preferably, the tensioners are formed integrally with the valve flaps when molded and are preferably diametrically aligned on opposite sides of the valve. Further, preferably, the tensioners are permanently under compression upon assembly of the valve in the valve housing. As a result of the tensioners, the valve flaps are pressed against each other by the tensioners to create a barrier that prevents blood or air transmission through the valve slit. When the dilator is removed from the valve and the sheath, an audible indication assures the practitioner that the valve is sealed.

The present invention is also a valve and/or a valve/valve housing arrangement as described above, for use in a medical device requiring a self-sealing valve, in addition to tearaway introducer sheaths.

In a particular embodiment of a valve of the present invention, each tensioner may comprise two lateral stands having a central hollow formed between the two stands. Each tensioner lateral stand has an inward section abutting a respective valve flap, and an outward section adjacent the valve housing side wall, joining each other adjacent the central hollow at an angle less than 180°; such an angle provides for the tensioners to buckle outwardly on both sides of the central hollow, rather than buckle both in the same direction when the dilator or catheter is disposed through the valve. In another embodiment of valve, the tensioners are tubular in shape.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
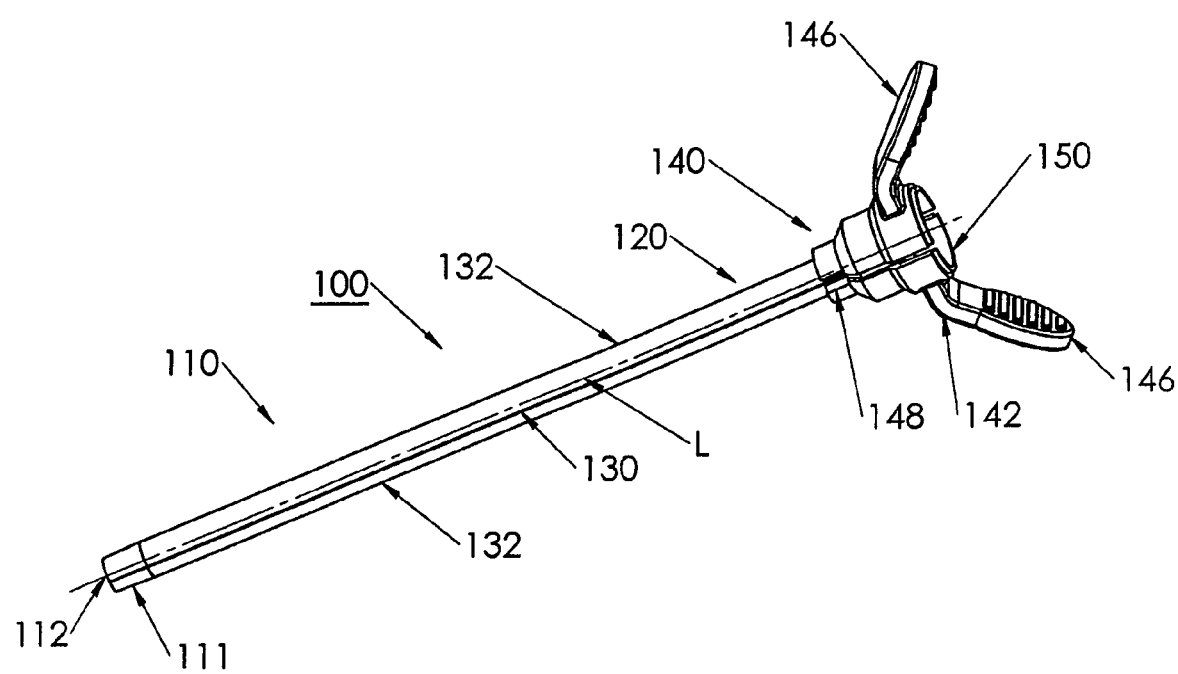
FIG. 1 is an isometric view of a tearaway sheath tube and hub of the present invention.

In the drawings, like numerals indicate like elements throughout. Certain terminology is used herein for convenience only and is not to be taken as a limitation on the present invention. The terms "distal" and "proximal" refer, respectively, to directions closer to and away from a tip of an introducer sheath to be inserted into an incision. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

FIG. 1 shows a tearaway catheter introducer sheath assembly 100 having a distal sheath tube portion 132 and a proximal sheath hub portion 140, and defining a longitudinal axis L therealong. The sheath tube 132 is a hollow tube with a narrowing distal tip 111 at its distal end, with a distal opening 112 therethrough. A tear seam is defined on the sheath tube portion 132, such as a pair of score lines 130 formed along the opposing sides of the sheath tube portion 132 along the entire length thereof, allowing the sheath tube portion to be peeled apart into two pieces along the tear seam 130 at the time of sheath removal from a catheter (not shown) that has been inserted through the sheath assembly into the venotomy. The sheath hub portion 140 is firmly affixed to the proximal end of the sheath tube portion 132 and has a proximal opening 150 accessing the central passageway of the sheath tube portion 132 that allows the insertion of a dilator and a catheter (neither shown), successively, through the sheath assembly.

The sheath hub portion 140 consists of two half-portions 142, that preferably are identical and are affixed to the sheath tube portions on each side of the tear seam 130 and are preferably joined to each other along an interface, preferably by being molded as an integral hub unit. A plane of separation is defined between the two hub half-portions, such as a pair of opposed V-grooves 148, or pair of opposed arrays of reveals, aligned with the tear seam 130 of the sheath tube portion, allowing the clean separation of the introducer sheath assembly 100 into two halves for its removal from a catheter. Each of the hub half-portions further comprises a tab 146 that is manually grippable to facilitate handling and orientation of the introducer sheath assembly 100 by a practitioner and also provide gripping surfaces for eventually prying the hub half-portions apart for peeling the introducer sheath away from a catheter.

Figure 2:
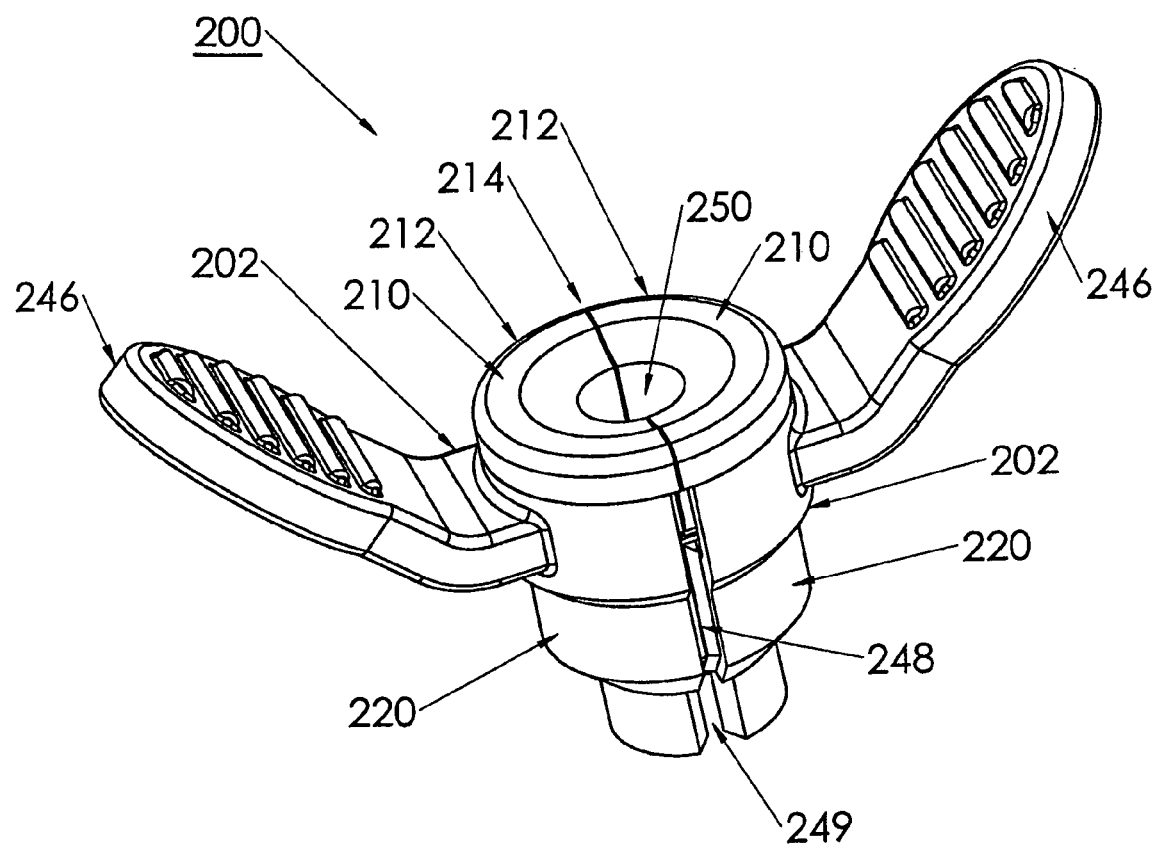
FIG. 2 is an isometric view of the present invention's sheath hub with integrated hemostasis valve disposed therewithin and having retention cap members affixed to the hub.
Figure 3:
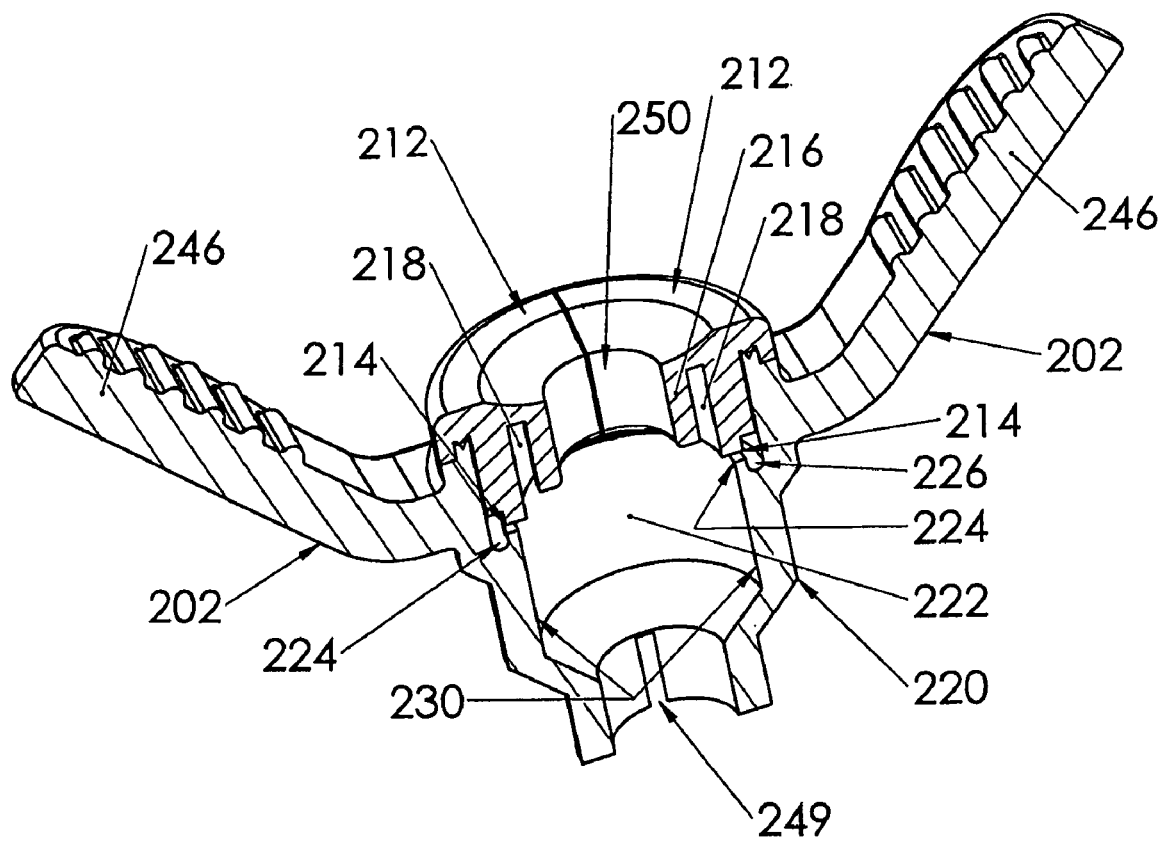
FIGS. 3 and 4 are cross section views of the sheath hub and cap members of FIG. 2 with the integrated hemostasis valve removed and with the valve in position therein, respectively.

FIG. 2 is an isometric view of the sheath hub 200 of the present invention, having therewithin an integrated hemostasis valve (see FIGS. 4 to 7). In FIGS. 2 and 3, the sheath hub 200 comprises a retention cap 210 affixed to its proximal end, and a valve housing 222 along its distal portion 220 adjoining the sheath tube (FIG. 1). The retention cap preferably comprises a pair of cap halves 212 that are not joined to each other but that are affixed firmly to the proximal end of the sheath hub 200, to respective ones of the sheath hub half-portions 202 and having an interface gap therebetween along a plane of separation. Tabs 246 are integrally joined to the respective hub half-portions 202, in one configuration, although the configuration of the tabs is optional and does not affect the functionality of the present invention, nor limit the scope of the claims. A hollow passage is formed through the entire longitudinal length of the hub 200 between a proximal opening 250, and a distal opening that communicates with the passageway of the sheath tube portion. A plane of separation intersects the hub at lines of separation or weakness such as V-grooves 248 that extend along the exterior surface of hub 200 between the hub half-portions, and optionally longitudinal arrays of reveals 249 may be selectively utilized, or both as shown, that will align with the tear seam of the sheath tube portion. In one method of manufacturing, the hub is insert-molded directly to the proximal end of the sheath tube.

Figure 4:
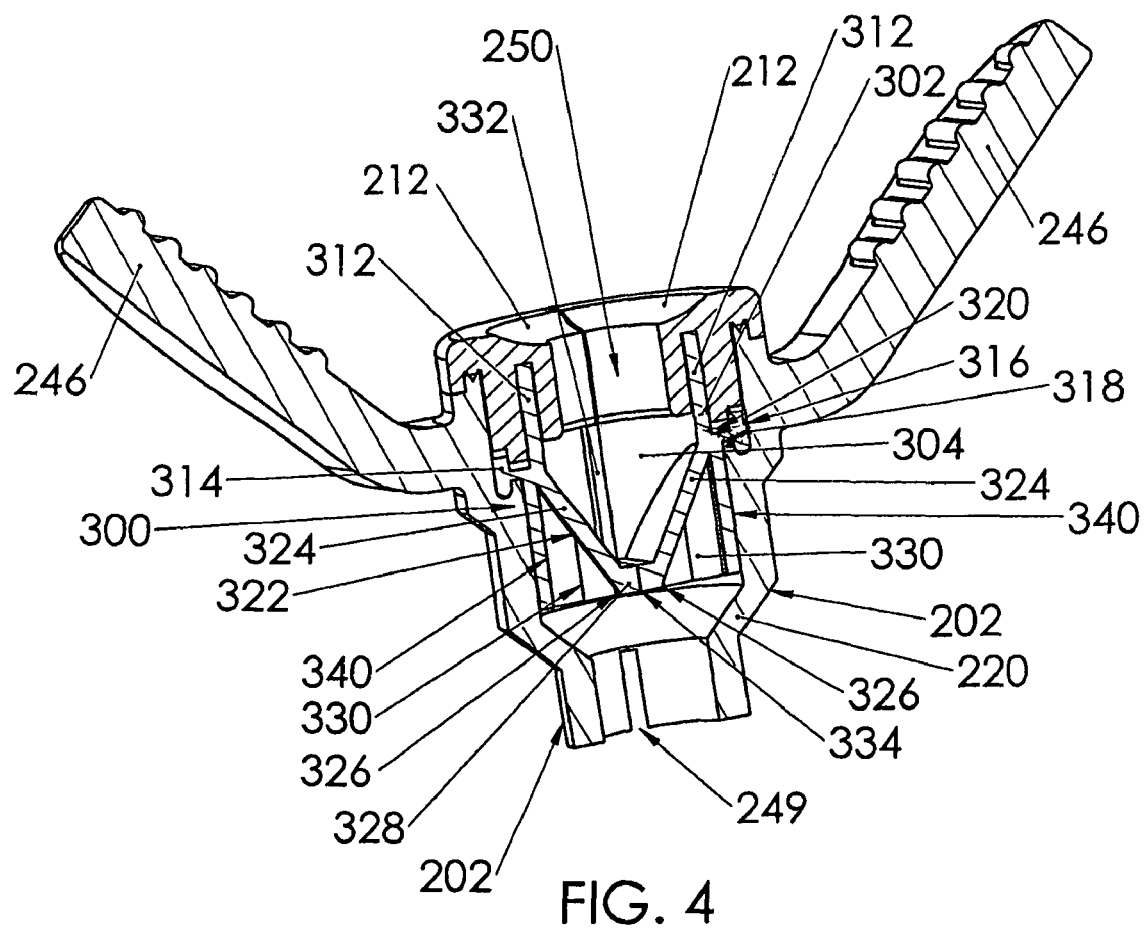
Figure 5:
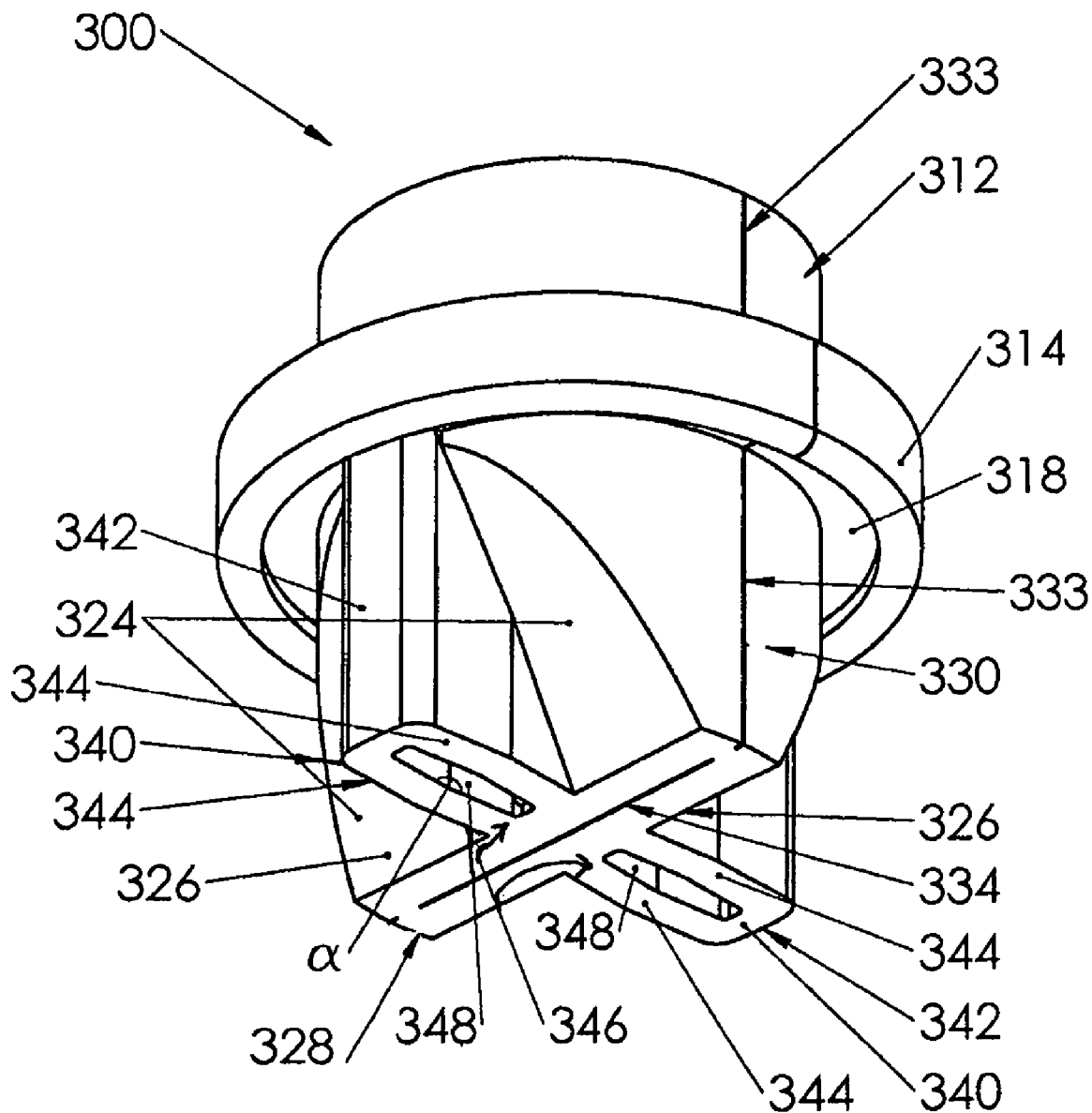
FIGS. 5 to 7 are, respectively, an isometric view, a first elevation view (in cross-section) and a second elevation view rotated 90° from the first along the longitudinal axis, of the valve of the present invention.
Figure 6:
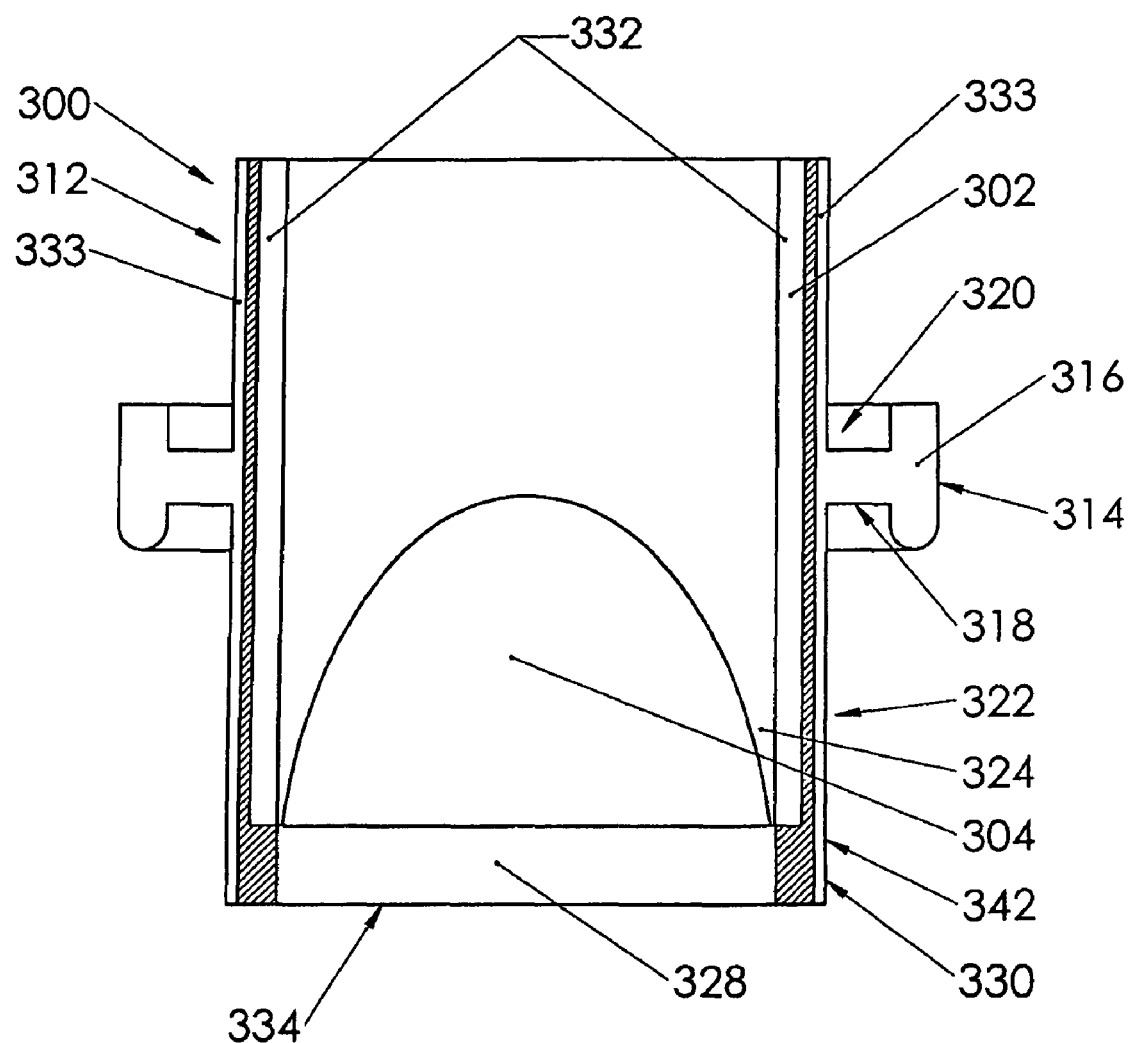
Figure 7:
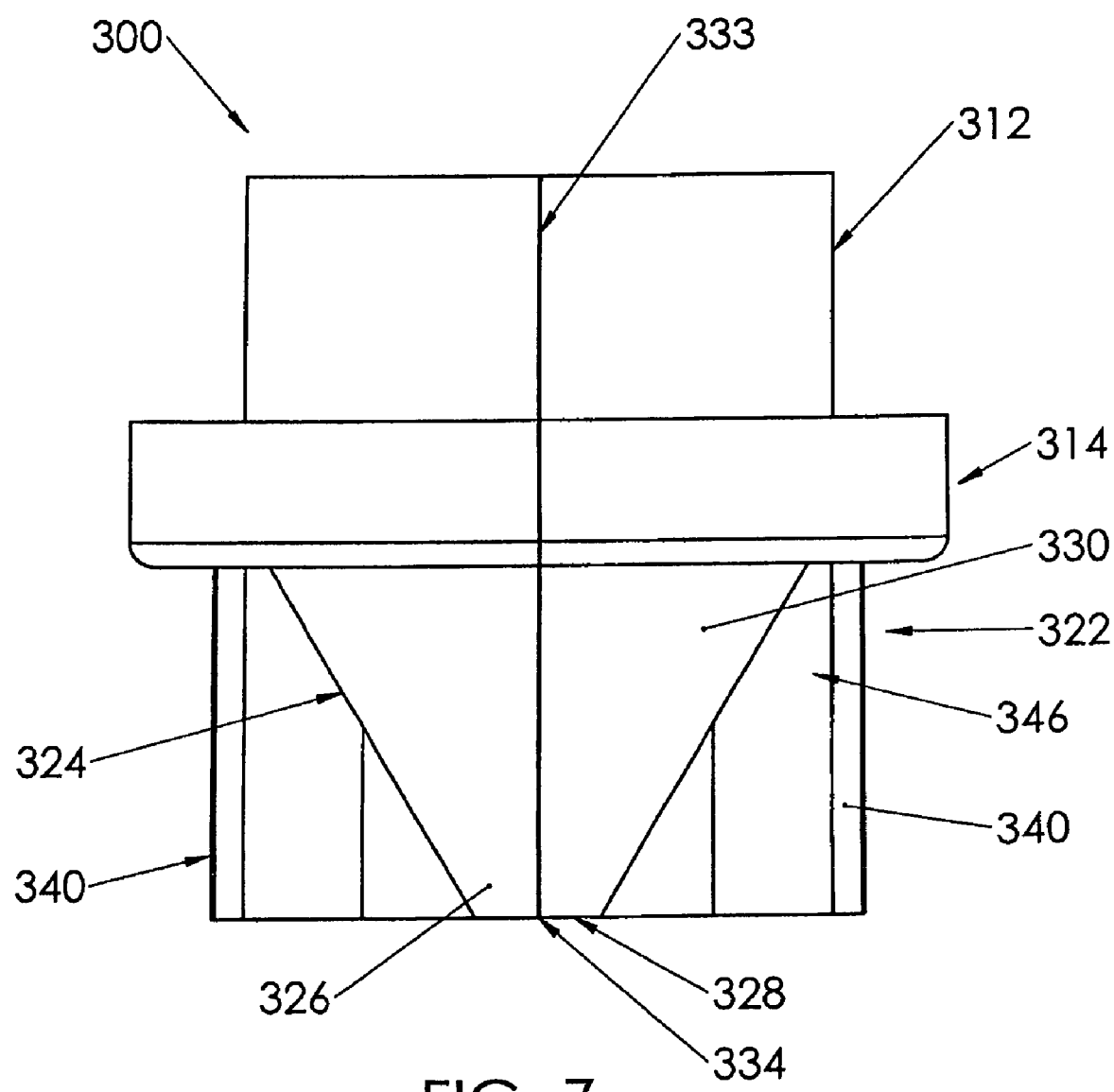

A cross sectional view of the hub 200 of FIG. 2 is presented in FIGS. 3 and 4, without and with a valve 300 in position, respectively, with the cross section taken at 90° angular distance from the plane of separation to illustrate the V-grooves and reveals 248,249. The hub half-portions 202 are seen to be identical, and provide therebetween a central chamber defining a valve housing 222 to accommodate valve 300. A pair of identical retention cap half members 212 are also shown affixed to the sheath hub 200 in both figures, with a cap interface gap being aligned with the V-grooves (FIG. 2) and reveals 249 of the hub 200. Hub 200 includes a short annular flange 224 extending proximally beside the valve housing and defining outwardly thereof a groove 226 for a corresponding annular flange of valve 300; correspondingly, the cap half members 212 each have a short outer semi-circular flange 214 extending distally opposing the hub annular flange 224, also for a corresponding annular flange of valve 300. Cap half members 212 each further include an elongated inner semi-circular flange 216 extending distally to define outwardly thereof a deep groove 218 for a corresponding elongated annular flange of valve 300.

Valve 300 is seen in FIGS. 4 to 7. In FIG. 4, the valve is sectioned along a plane perpendicular to the plane of separation of the sheath hub, and is shown completely in FIG. 5; in cross-section along the plane of separation in FIG. 6; and in an elevation view in FIG. 7. Valve body 300 comprises a cylindrical side wall 302 encircling a center valve passage 304, and including a proximal valve portion 312 consisting of an elongated axially extending annular flange, a radially outward annular ring portion 314 intermediate the proximal and distal ends of the valve, and a distal portion 322. The annular ring portion 314 includes an outer axially oriented ring section 316 defining inwardly thereof distal and proximal annular grooves 318,320. The distal portion 322 comprises a pair of essentially flat distally extending opposed wall portions or valve flaps 324 that extend from the location of the ring portion 314 and converging to respective distal ends 326 that are joined together by a flat land 328 defining a valve distal tip. Side edges of the valve flaps 324 are integrally joined to each other by side wall portions 330 to surround the center passage 304 until the valve flaps converge at flat land 328. A plane of separation intersects the valve at lines of separation or weakness such as a pair of tear seams or V-grooves 332 defined into opposing sides of the valve from its proximal end to its distal end, preferably along its interior surfaces, and defining valve half-portions; the annular ring 314 is also cut aligned with V-grooves 332. Optionally, a score line 333 is provided on the exterior valve surface co-aligned with V-grooves 332 along the interior surface, resulting in a thin web of material between the slits and the V-grooves such as between 0.006 to 0.008 inches in thickness (0.152 to 0.203 mm). A virtual opening, such as preferably a slit 334, is cut or formed through the flat land 328, extending from side to side but not through the ends of the flat land 328, with the slit being aligned with V-grooves 332.

The valve 300 is seated in the valve housing, by the distal portion 322 extending distally of the annular flange 224 of the hub portions, with the annular flange 224 received into associated distal groove 318 of the ring portion of the valve, and the distally extending end of outer section ring 316 being received into groove 226 of the hub. Each cap half member 212 is affixed to the hub with its elongate inner flange 216 received within proximal valve portion 312 and elongate proximal valve portion 312 received into deep groove 218. Further, the outer flange 214 of each cap half member is received into associated proximal groove 320 of ring section 316 of valve 300. The cap half members 212 preferably are bonded or welded in place (or, optionally, snapped in place) to the respective hub half-portions at overlapping flanges between the proximal hub end and the outer periphery of the distal face of the cap half members. Preferably, the ring portion 316 of valve 300 is preferably under compression. The valve 300 thus seals the proximal opening of the valve housing 222 defined in the sheath hub 200. The proximal opening 250 of the sheath assembly is preferably only just slightly larger than the outer diameter of the dilator and the catheter to further reduce the possibility of blood loss, and to aid in alignment.

The valve 300 is preferably made of elastomeric material such as silicone elastomer, but may be of other materials, such as isoprene. As such, the valve returns to its original formed shape after deformation by mechanical force. The insertion of a dilator through the valve and through slit 334 pushes the valve flap ends 326 to the side thereby allowing passage of the dilator therethrough. The valve flap ends 326 forming the flat land 328, wrap around the dilator and minimize the space between the dilator body and the valve body 300. When the dilator is removed, the flexibility of the valve flaps allows the valve to close and reduce the chance of blood loss or air embolism.

The valve and valve arrangement of the present invention is further improved when tensioners 340 are added to the valve body 300, which cooperate with interior surface 230 of the valve housing to increase the closing force of the valve flaps 324. A valve tensioner 340 is located on the exterior of each of the valve flaps 324 between the pair of side sections 328 of each valve flap and is so dimensioned and shaped for exterior faces 342 of the tensioners to bear against the interior valve housing surface 230 upon assembly. Preferably, for ease of manufacturing, the tensioners may be integrally molded portions of the valve body 300 and of the same flexible material. By bearing against the valve housing wall 230, the tensioners assert force against the walls of the valve flaps therealong to increase the closing force of the valve flap distal ends 326 at slit 334. To assure that the exterior faces 342 bear against the valve housing walls upon assembly, the length of the lateral side walls 344 of each tensioner are dimensioned to be slightly larger than the distance between the valve flaps 324 and the valve housing wall, allowing the tensioners to be pre-stressed when placed.

The tensioners depicted in FIGS. 4 to 7 preferably comprise a pair of opposing lateral stands or side walls 344 joined at an inner joint at interior ends 346 and at an outer joint at exterior faces 342, and between the pair of lateral stands is an elongate hollow center space 348. The inner surfaces of the lateral stands 344 can be partitioned conceptually into a first surface that is adjacent interior end 346 and a second surface adjacent to exterior face 342. An angle $\alpha$ is preferably formed into the inner surfaces of the lateral stands 344 which are the side walls of the hollow center opening, at a medial location between the inner and outer joints, such that each lateral side wall can be said to have two wall portions that meet at that location; the angle is less than 180° although more than 90°, such as between 179° and 160°. The advantage of this configuration is that when the valve flaps 324 are urged outwardly by the dilator, the lateral stands 344 of the tensioners 340 will buckle apart outwardly from the hollow center space 348 thereby allowing the valve flaps 324 to move freely and predictably.

Because of the positive pressure asserted on the valve flaps 324 by the pre-tensioned or pre-stressed tensioners 340, when the valve flaps 324 close as a result of removing the dilator, an audible indicator sound is produced and signals to the practitioner that the valve has closed and has sealed the passage.

Figure 8:
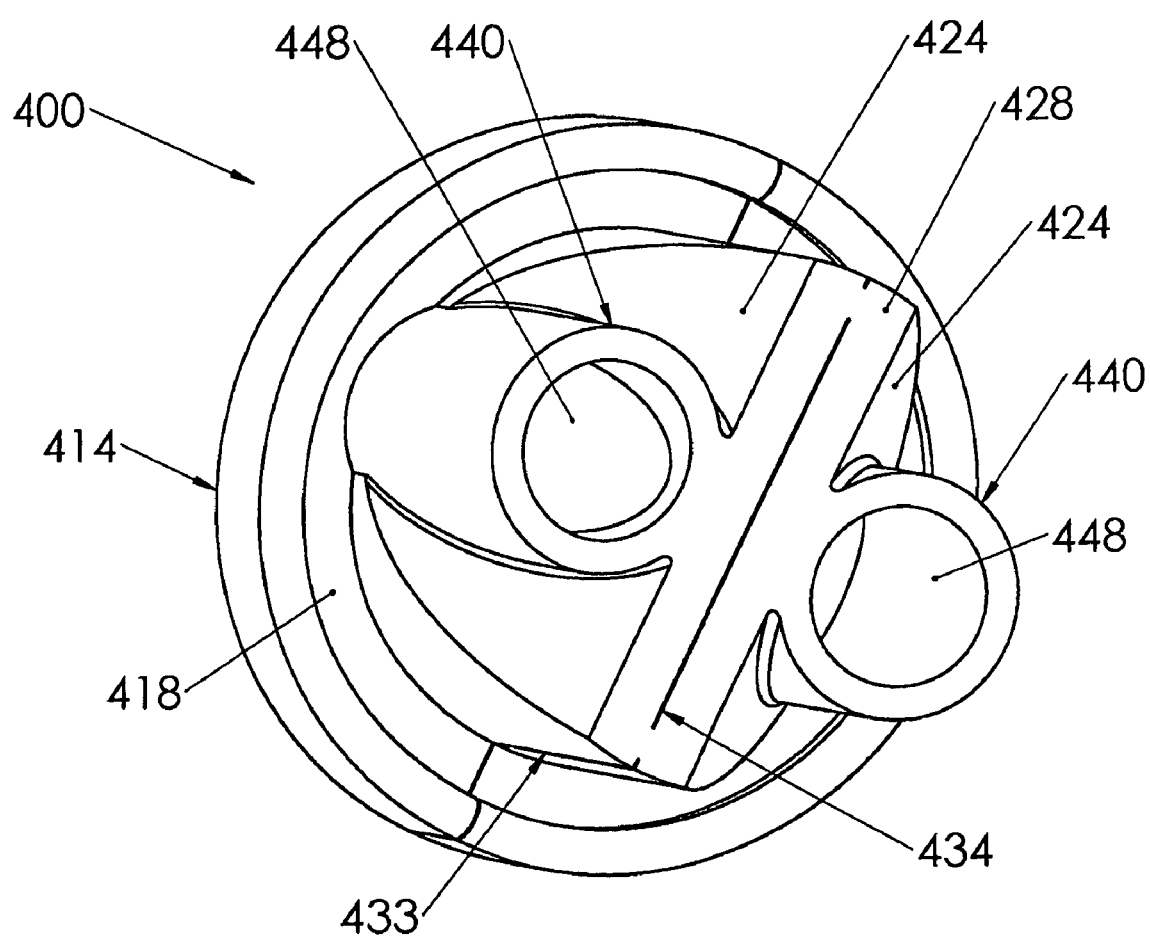
FIG. 8 is an isometric view of another valve embodiment wherein the tensioners are tubular.

A second valve embodiment 400 is shown in FIG. 8. Valve 400 includes an annular ring 414 defining a distal groove 418, opposed outer slits 433 and opposed flaps 424 extending to a distal flat land 428 having a slit 434. Tensioners 440 are shown to be tubular in shape, with a circular central opening 448; tensioners 440 act similarly to tensioners 340 of FIGS. 4 to 7.

While the valve and valve arrangement of the present invention has been described in relationship to a tearaway introducer sheath for a catheter, the valve and valve arrangement with its enhanced self-closing capability may easily be utilized in other medical devices such as a guidewire introducer assembly or a port, in which case the valve need not have V-grooves to facilitate being split.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A hemostasis valve for assembly within a medical device, comprising:
    a valve body having a proximal cylindrical end, a distal end portion and a central passage extending from the proximal end to a distal end,
    the distal end including a pair of distally extending opposed side walls converging at distal ends forming a distal tip having a virtual opening therethrough, and
    the valve body further including a pair of tensioners projecting radially outwardly from side sections of the respective distally extending opposed side walls to exterior tensioner faces for engaging an interior wall of a valve housing defined in the medical device within which the valve body is disposed,
    wherein each tensioner comprises two lateral sidewalls coextending between an outer joint at a common exterior end and an inner joint at the distally extending opposed side walls of the valve body, defining a radially elongate hollow center opening therebetween,
    whereby the tensioners bear against the interior valve housing wall to press the distally extending side walls toward and against each other at the distal tip to close the virtual opening either completely in a sealing fashion or sealingly against outer surfaces of another medical device inserted through the valve's central passage and virtual opening.

2. The hemostasis valve of claim 1 wherein the virtual opening is a slit extending across most of the distal valve tip.

3. The hemostasis valve of claim 1 wherein the tensioners are integrally formed with the valve body.

4. The hemostasis valve of claim 1 wherein side walls of the hollow center opening each have first and second portions that are joined at an angle less than 180° and greater than 90° at a medial location between the inner and outer joints.

5. The hemostasis valve of claim 4 wherein the angle is between 179° and 160°.

6. The hemostasis valve of claim 1, further including a valve housing defined in a medical device, the valve housing having an interior wall surface.

7. The hemostasis valve of claim 6 wherein the tensioners are so shaped and dimensioned with respect to the valve housing as to bear against the interior wall surface thereof upon and after assembly, thereby pressing the distally extending opposed side walls of the valve body together at the valve's distal tip, creating a barrier restricting flow of blood and air through the valve body.

8. The hemostasis valve of claim 7 wherein the tensioners are so shaped and dimensioned as to be so pre-stressed against the interior wall surface of the valve housing as to produce an audible indicator sound when a dilator previously extending through the virtual valve opening is removed therefrom.

9. A hemostasis valve for assembly within a medical device, comprising:
    a valve body having a proximal cylindrical end, a distal end portion and a central passage extending from the proximal end to a distal end,
    the distal end including a pair of distally extending opposed side walls converging at distal ends forming a distal tip having a virtual opening therethrough, the pair of sidewalls each having a valve flap with a distance between the valve flaps, and
    the valve body further including a pair of tensioners projecting radially outwardly from side sections of the respective distally extending opposed side walls to exterior tensioner faces for engaging an interior wall of a valve housing defined in the medical device within which the valve body is disposed,
    whereby the tensioners bear against the interior valve housing wall to press the distally extending side walls toward and against each other at the distal tip to close the virtual opening sealingly against outer surfaces of another medical device inserted through the central passage of the valve body and virtual opening and therebeyond,
    wherein each tensioner comprises two lateral side walls that each have a radially outward length that is slightly larger than the distance between the valve flaps and the valve housing wall so as to bear against the interior wall surface thereof upon and after assembly, thereby pressing the distally extending opposed side walls of the valve body together at the distal tip of the valve either against the other medical device or against each other, creating a barrier restricting flow of blood and air through the valve body.

10. The hemostasis valve of claim 9 wherein the tensioners are so shaped and dimensioned as to be so pre-stressed against the interior wall surface of the valve housing as to produce an audible indicator sound when the medical device previously extending through the virtual valve opening is removed therefrom.

11. The hemostasis valve of claim 10 wherein each tensioner comprises a tubular shape.

* * * * *